United States Patent
Sharafat et al.

(10) Patent No.: US 9,687,213 B2
(45) Date of Patent: Jun. 27, 2017

(54) METHOD AND APPARATUS FOR REAL-TIME AND ROBUST STRAIN IMAGING

(71) Applicants: Ahmad R. Sharafat, Edmonton (CA); Saeed Rezajoo, Edmonton (CA)

(72) Inventors: Ahmad R. Sharafat, Edmonton (CA); Saeed Rezajoo, Edmonton (CA)

( * ) Notice: Subject to any disclaimer, the term of this patent is extended or adjusted under 35 U.S.C. 154(b) by 52 days.

(21) Appl. No.: 14/923,108

(22) Filed: Oct. 26, 2015

(65) Prior Publication Data

US 2017/0112470 A1  Apr. 27, 2017

(51) Int. Cl.
| | |
|---|---|
| *A61B 8/08* | (2006.01) |
| *G06T 7/00* | (2017.01) |
| *G06K 9/46* | (2006.01) |
| *A61B 8/00* | (2006.01) |
| *A61B 8/14* | (2006.01) |
| *A61B 5/055* | (2006.01) |
| *A61B 5/00* | (2006.01) |

(52) U.S. Cl.
CPC .......... *A61B 8/485* (2013.01); *A61B 8/14* (2013.01); *A61B 8/403* (2013.01); *A61B 8/463* (2013.01); *A61B 8/5223* (2013.01); *G06K 9/4604* (2013.01); *G06T 7/0012* (2013.01); *G06T 7/0079* (2013.01); *A61B 5/055* (2013.01); *A61B 5/7282* (2013.01); *A61B 5/7425* (2013.01); *G06T 2207/10088* (2013.01); *G06T 2207/10132* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 7,949,498 B2 * | 5/2011 | Walker | G06T 7/30 345/606 |
| 2004/0215075 A1 * | 10/2004 | Zagzebski | A61B 8/00 600/442 |
| 2007/0167772 A1 * | 7/2007 | Radulescu | A61B 8/08 600/438 |
| 2007/0234806 A1 * | 10/2007 | Jiang | A61B 8/485 73/570 |

(Continued)

OTHER PUBLICATIONS

Lujie Chen et al: A Hybrid Displacement Estimation Method for Ultrasonic Elasticity Imaging; IEEE Trans Ultrason Ferroelectr Freq Control 57; Apr. 2010; p. 866-882.

(Continued)

*Primary Examiner* — Tsung-Yin Tsai
(74) *Attorney, Agent, or Firm* — Anthony R. Lambert

(57) ABSTRACT

A robust algorithm is disclosed for real-time strain imaging. The method can be implemented on conventional medical imaging modalities such as ultrasound, MRI, etc. The pre- and post-deformation images, acquired by an imaging system, are used by the algorithm to produce the strain map. Deformation can be performed by any available means, such as an existing part of the imaging device (as in freehand elastography) or a separate compression fixture. Due to the computational efficiency of the algorithm, any conventional processing platform, including personal computers, tablet PCs, and smart phones can be employed for strain imaging, to construct an ultra-portable strain imaging system.

20 Claims, 8 Drawing Sheets

(56) References Cited

U.S. PATENT DOCUMENTS

| | | | | |
|---|---|---|---|---|
| 2008/0144902 A1* | 6/2008 | Radulescu | ............ | G06T 7/238 382/130 |
| 2010/0134629 A1* | 6/2010 | Lindop | .................. | A61B 8/08 348/163 |
| 2010/0256494 A1* | 10/2010 | Azuma | .................. | A61B 8/08 600/443 |
| 2011/0172538 A1* | 7/2011 | Sumi | ...................... | A61B 8/06 600/453 |

OTHER PUBLICATIONS

Hassan Rivaz: Real-Time Regularized Ultrasound Elastography; IEEE Trans. Med. Imag; 30: p. 928-945; 2011.

* cited by examiner (a)          (b)

(a)          (b)

(a)       (b)

(a)       (b)

METHOD AND APPARATUS FOR REAL-TIME AND ROBUST STRAIN IMAGING

TECHNICAL FIELD

Elasticity imaging, medical imaging.

BACKGROUND OF THE INVENTION

Cancer is a leading cause of death in the world. According to the World Health Organization (WHO), about 8.2 million people died because of cancer in 2012, 70% of whom were living in developing countries. The number of cancer cases is expected to rise from 14 million in 2012 to 22 million in the next two decades.

Screening is widely accepted as an effective strategy for early detection of cancer, which can increase the rate of successful treatment. However, false positive alarms are common in screening, leading to significant unnecessary costs and psychological burdens in such cases. One major instance is screening the breast cancer, which is the most fatal cancer among women, causing more than 500,000 deaths worldwide in 2012.

Breast cancer screening is usually performed via mammography and clinical breast examination. However, similarities between physical and mammographic symptoms of benign and malignant lesions result in many false positive alarms. In such cases, benign lesions are unnecessarily chosen for biopsy. The limitations of mammography have been mentioned by many investigators, including Gøtzsche and Nielsen "Screening for breast cancer with mammography," Cochrane Database Syst. Rev. 2013; 6:CD001877, whose observations of 600,000 women screened by mammography during 10 years showed that for every 2000 women, one's life would be extended, 10 healthy women would be unnecessarily treated, and 200 women would suffer intense psychological stress due to false positive alarms. Such deficiencies have motivated research to develop more efficient screening strategies.

Palpation of suspicious tissues has long been practiced by physicians to differentiate malignant tumors from benign lesions. Although this technique is limited to size and depth of diagnosed lesions, palpation lies on a simple yet useful physical principle: malignant lesions are much "stiffer" than benign ones. The concept of stiffness is closely related to elasticity, which has been widely studied in physics, and is the basis of an emerging medical imaging modality called "elastography". The aim of this method is to provide more detailed and practical description of stiffness and other mechanical properties of tissues, which are independent from anatomical properties extractable from conventional medical images. Clinical studies of elastography, such as the work by Garra, et al "Elastography of breast lesions: initial clinical results", Radiology 1997; 202:79-86, showed promising results in differentiating benign from malignant lesions, not only by distinguishing the difference in stiffness, but also due to the larger appearance of malignant tissues in elastograms (i.e., elasticity images), which is believed to be the consequent of desmoplastic reaction around malignant tissues. Several tissues have been imaged by elastography, including breast, prostate, thyroid, pancreas, lymph nodes, liver, kidney, etc.

Elasticity is defined as the tendency of tissues to resume their original size and shape, after being deformed by an applied "stress" (i.e., force acting on unit area). Hence, elasticity imaging requires analyzing two data sets corresponding to the pre- and post-deformation states of tissues. The "displacement" of tissues is estimated by comparing the pre- and post-deformation data. Depending on the application, the desired elasticity parameters are extracted from the displacement map.

Theoretically, any imaging modality can be used for displacement estimation. But due to practical limitations for medical imaging, only ultrasound and magnetic resonance imaging (MRI) systems have been utilized for this purpose so far. Since ultrasound is much less costly than MRI and is capable of real-time imaging, ultrasound elastography is more frequent in clinical applications. Specifically, a very cost-efficient technique, called "freehand elastography" (or quasi-static elastography), can be implemented on ordinary ultrasound imaging systems without any major hardware modification. In this technique, tissues are gently compressed by the ultrasound transducer, with such a low velocity that static mechanics can be assumed. In some applications, natural compression sources such as arterial pulsation or patient breathing, are utilized instead of the transducer for tissue deformation. Ultrasonic RF signals are acquired as tissues are compressed, via the same transducer performing the compression. The displacement of tissues is estimated by comparing pre- and post-deformation RF echoes. By taking the spatial derivative of displacement, "strain" distribution is obtained, which is the ratio of change in the length of tissues (due to the applied stress) to their original length. The strain map is displayed in a grayscale or colored image. Stiffer regions compress less than softer ones. Hence, they exhibit lower strain values. In other words, strain maps illustrate a relative stiffness distribution of tissues. Usually, the strain is kept lower than a few percent, resulting in sufficiently small displacements to preserve the similarity between pre- and post-deformation echo signals.

The cost saving in freehand elastography comes at the expense of some limitations. First, strain should be almost uniform to interpret the image, which implies that the compression must be performed carefully. However, the tendency of objects for out-of-plane motion makes it difficult to perform such compression, especially for deeper organs that are less influenced by the applied stress. These limitations can greatly degrade the quality of strain maps. The majority of elasticity imaging systems in which strain maps are generated offline, resolve this issue by collecting several input RF frames to make sure that acceptable frames are obtained. However, this approach is too time-consuming for busy clinical practice. The alternative is real-time strain imaging, which provides instant feedback to the operator to facilitate obtaining higher quality images. This technique also enables side-by-side (or overlaid) display of strain and real-time ultrasonic B-scan images for easy assessment of observed structures. However, due to the fact that calculations are minimized in real-time processing, real-time algorithms may suffer from lack of quality and robustness as compared with offline strain imaging methods. More specifically, they are more vulnerable to "signal decorrelation", which is defined as the lack of correlation between pre- and post-deformation signals, caused by increasing the applied stress.

A few real-time displacement estimation techniques have been proposed to overcome the decorrelation issue, which are mainly based on coarse-to-fine approaches and tracking strategies. For instance, an article by L. Chen, R. J. Housden, G. M. Treece, A. H. Gee, and R. W. Prager, entitled "A hybrid displacement estimation method for ultrasonic elasticity imaging," IEEE Trans. Ultrason. Ferroelect. Freq.

Contr., 57:866-882, 2010, which is incorporated by reference herein, proposed a multi-level approach where the precision of displacement estimation was gradually increased and the displacement map was spread from the most qualified regions to the other parts. However, the decorrelation issue at the first step of the algorithm could affect the entire displacement estimation process in this approach.

Another notable work is reported in an by article H. Rivaz, E. M. Boctor, M. A. Choti, and G. D. Hager, entitled "Real-time regularized ultrasound elastography," IEEE Trans. Med. Imag., 30:928-945, 2011, which is incorporated by reference herein. Rivaz et al. proposed a regularized algorithm named "Analytical Minimization" (AM) which provided the displacement estimation with subsample precision for a "seed line" of the RF frame, and propagated the estimation through adjacent lines to other parts of the displacement map. Although the regularization enhances the robustness of the algorithm against signal decorrelation, this issue can still affect the accuracy of the results through the seed line, where inaccurate estimation would spread to the whole image.

There exists a need for a real-time strain imaging method and apparatus with appropriate imaging quality and robustness for ordinary clinical use, where the operator's concentration performing compression and data acquisition is not as high as that of laboratory conditions.

It is very desirable that the real-time strain imaging method and apparatus be developed in such a way to be independent of input data and imaging modality so that it can be utilized in any medical, industrial, or scientific application in which the study of elasticity is considered beneficial.

OBJECTS OF THE INVENTION

Based on the aforementioned discussions, it is a main object of the present invention to provide a method and apparatus for real-time strain imaging with improved robustness against the major sources of data decorrelation, specifically variations in the applied compression due to the slips of operator's hand during freehand elastography.

It is another object of this invention to provide a computationally efficient method and apparatus for real-time strain imaging that can be implemented on conventional ultrasound imaging systems, personal computers, tablets and/or smart phones.

It is also another object of this invention to provide a method and apparatus for study of elasticity by way of real-time strain imaging, in which pre- and post-deformation images are obtained from any imaging modality in any medical, industrial, or scientific application.

SUMMARY OF THE INVENTION

Accordingly, there is provided a method and apparatus to overcome at least one or more of the aforementioned limitations in real-time strain imaging. There is provided a method and apparatus for estimating displacement and strain in elastic materials. The computational cost of the method is sufficiently low for real-time and robust implementation on conventional ultrasound imaging systems, personal computers, tablets and/or smart phones.

The method employs a multi-step coarse-to-fine hierarchical displacement estimation by average downsampling the input data to accelerate the processing speed. At each step, input images are divided into blocks and the displacement of each block is estimated through block matching approach. The downsampling rate and size of the blocks are decreased as the algorithm proceeds through the steps, so that both the estimation precision and speed are preserved. Averaging the data prior to downsampling reduces the noise effect and enhances the information provided by the downsampled data.

The method gradually limits the processed region of input images by detecting the most qualified blocks and focusing on the neighboring areas of these blocks to find a seed line for the displacement map. Hence, as the size of input data is increased through reduction of downsampling rate, the processed area is shrank to improve the efficiency of the method.

The method spreads the displacement map from the seed line to the neighboring areas until the whole image is obtained. Since the quality of the seed line is the highest in the image, this approach improves overall imaging quality.

The method calculates displacement of the seed line at integer precision through coarse-to-fine approach. Subsample displacement of the line is then estimated by the aforementioned AM method, proposed by Rivaz et al., and is propagated to the whole displacement map. Hence, this method maintains the precision of displacement estimation.

The method and apparatus provides a map of the strain distribution of an object by first estimating the displacement map and then calculating the spatial derivatives of displacements. In order to obtain the displacement distribution, at least two images corresponding to the pre- and post-deformation states of the object are acquired by an imaging modality. In some of the preferred embodiments in which ultrasound imaging system is incorporated, either B-mode images constructed from envelope signals of the input RF echoes, or the original ultrasonic RF images can be used as the input data.

In some embodiments, the strain map is displayed in grayscale, which has been found to facilitate recognizing the details of the map for the human vision. Such representation is particularly useful when real-time ultrasound B-mode image is displayed side-by-side the strain map. In this case, both are displayed in grayscale so that the details of the B-mode image and the strain map can be assessed simultaneously.

In some embodiments, specifically where the display screen size is small, the strain map is represented in color, overlaid on the grayscale B-mode image, so that both can be displayed simultaneously in the whole screen and distinguished by the representation mode of each one. This is similar to color flow imaging in sonography, where blood velocity information is presented as a color-coded overlay on the B-mode image.

It is broadly hypothesized that benign and malignant lesions appear differently in the strain map. Malignant lesions are presented large and clear, compared with those in the corresponding B-mode image, and can be easily distinguished from the surrounding area. On the other hand, benign lesions can hardly be visualized, and appear with the same size as those in the B-mode image. This is consistent with physiological findings, which expect malignant lesions to be much firmer than normal tissues, yielding high contrasts in strain maps. On the contrary, benign lesions are softer and more mobile than malignant ones, making them move freely along with normal tissues in the object while compression is applied. As a result, benign lesions are not easily distinguished from the surrounding normal tissues in the strain maps.

Consequently, at least some embodiments provide a cost-effective method and apparatus for differentiating malignant lesions from benign ones. Since the method is computationally efficient, it can be implemented on existing medical imaging modalities as a software upgrade, without a need for hardware modification. More specifically, in embodiments incorporating ultrasound imaging modality, input data can be acquired with no additional cost, utilizing the ultrasound transducer for tissue compression, or even natural compression sources such as arterial pulsation or patient breathing.

In a second aspect of at least some embodiments, the method and apparatus facilitate diagnosing suspicious lesions by providing real-time strain maps, which can be displayed side-by-side or overlaid on anatomical images, particularly real-time ultrasound B-mode images. Hence, the physiological characteristics of benign and malignant lesions can be clearly differentiated by comparing strain maps with the corresponding B-mode images.

In a third aspect of at least some embodiments, the method and apparatus improves the robustness of strain imaging, which is a certain limitation in current real-time strain imaging methods. The improved robustness allows higher decorrelation in input data to be tolerated. Decorrelation is mainly caused by increasing the level of applied compression to the tissues, and is a common problem in busy clinical settings where the level of practitioners' concentration is reduced. Higher robustness preserves the image quality in such conditions, which is essential for accurate malignancy detection.

Accordingly, there is provided apparatus for the implementation of mentioned aspects and embodiments, comprising an imaging device for acquiring input data, a processor for displacement and strain estimations, and a display unit for showing the resulting images.

Any of the existing medical imaging modalities, such as the ultrasound imaging system and potentially the magnetic resonance imaging or computerized tomography, can be incorporated as the imaging device. The imaging device may accompany an extra compression fixture, or an existing part of the device, e.g., the ultrasound transducer, can be used for object deformation. In some embodiments, natural compression sources like arterial pulsation may be utilized for this purpose.

In embodiments wherein medical imaging modalities are incorporated, the processing unit of the imaging device may be sufficient for real-time implementation of the required computations for displacement and strain estimations. Otherwise, conventional desktop or mobile computers may be incorporated.

Further aspects and features of the method and apparatus, including the results that demonstrate the advantages of the strain imaging method, are apparent in the accompanying figures and drawings, and partly are described and exemplified in the detailed description of the preferred embodiments and the claims. No part of this section or the exemplifications in the following description should be considered as a limitation on the definition of the present invention(s).

BRIEF DESCRIPTION OF THE DRAWINGS

For a more complete understanding of the invention, reference is made to the following description and accompanying drawings, in which.

DETAILED DESCRIPTION OF THE INVENTION

Figure 1:
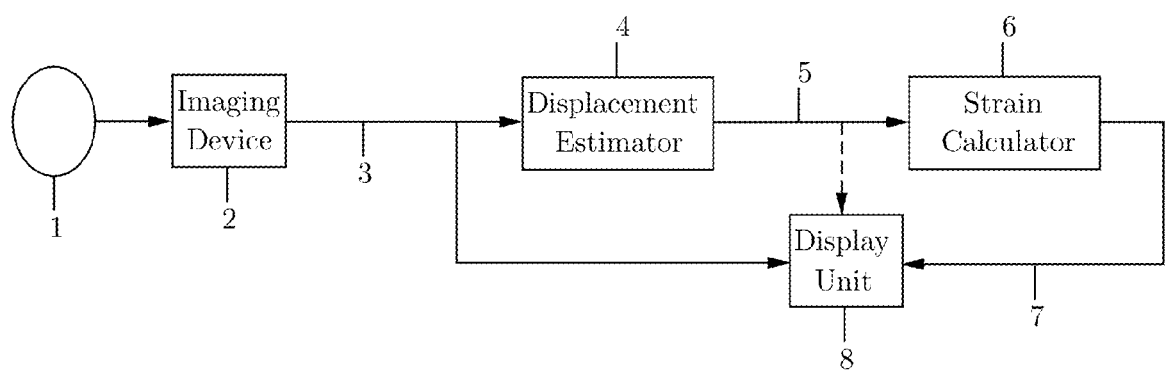
FIG. 1 shows a block diagram of strain image formation procedure in one embodiment of the present invention.

FIG. 1 shows a high-level block diagram of the strain map formation process of an object [1]. An imaging device [2] provides pre- and post-deformation images [3] of pre- and post-deformation states of the object [1]. The deformation may be performed by an external compression fixture, such as a mechanical arm; or a part of the imaging device [2] can be used for compressing the object [1], such as the transducer of ultrasound imaging system. In some applications, natural compression sources such as arterial pulsation, cardiac motion, or patient breathing may be utilized for object compression.

Theoretically, the imaging device [2] can be any type of imaging modalities. Currently, ultrasound imaging is most commonly practiced for elasticity imaging, and some preferred embodiments of the present invention are described with reference to ultrasonic data processing. However, other imaging systems such as, potentially, magnetic resonance imaging and computerized tomography may be employed for image acquisition.

The pre- and post-deformation images [3] acquired by the imaging device [2] form the input data of the displacement estimator [4], which generates the displacement map [5] of the object [1]. The displacement map [5] is then loaded into the strain calculator [6], which produces the final strain map [7], shown in the display unit [8]. The display unit [8] can be any kind of conventional display systems. The strain map [7] may be shown in grayscale or colored. Grayscale images are usually preferred in medical diagnosis, due to better visualization of the image details. If the size of the display unit [8] is sufficiently large and the pre- and post-deformation images [3] are generated in real-time, these images may also be displayed in grayscale, side-by-side the strain map [7]. If the display unit [8] size is small, the strain map [7] may be shown in color, overlaid on the pre- and post-deformation images [3] which are displayed in grayscale. In some applications where the displacement data may be of interest, the displacement map [5] can also be shown in the display unit [8].

The side-by-side presentation of both anatomical and elasticity images can significantly enhance the assessment of lesions by facilitating the comparison of anatomical and elastic properties of imaged tissues. Particularly, in embodiments wherein ultrasound imaging modality is incorporated as the imaging device [2], differentiating malignant tumors from benign lesions is significantly improved because malignant lesions have been found to appear much larger in the strain map than the ultrasound B-mode image, due to desmoplastic reaction. But benign lesions appear nearly the same size in both the B-mode image and the strain map.

Figure 2:
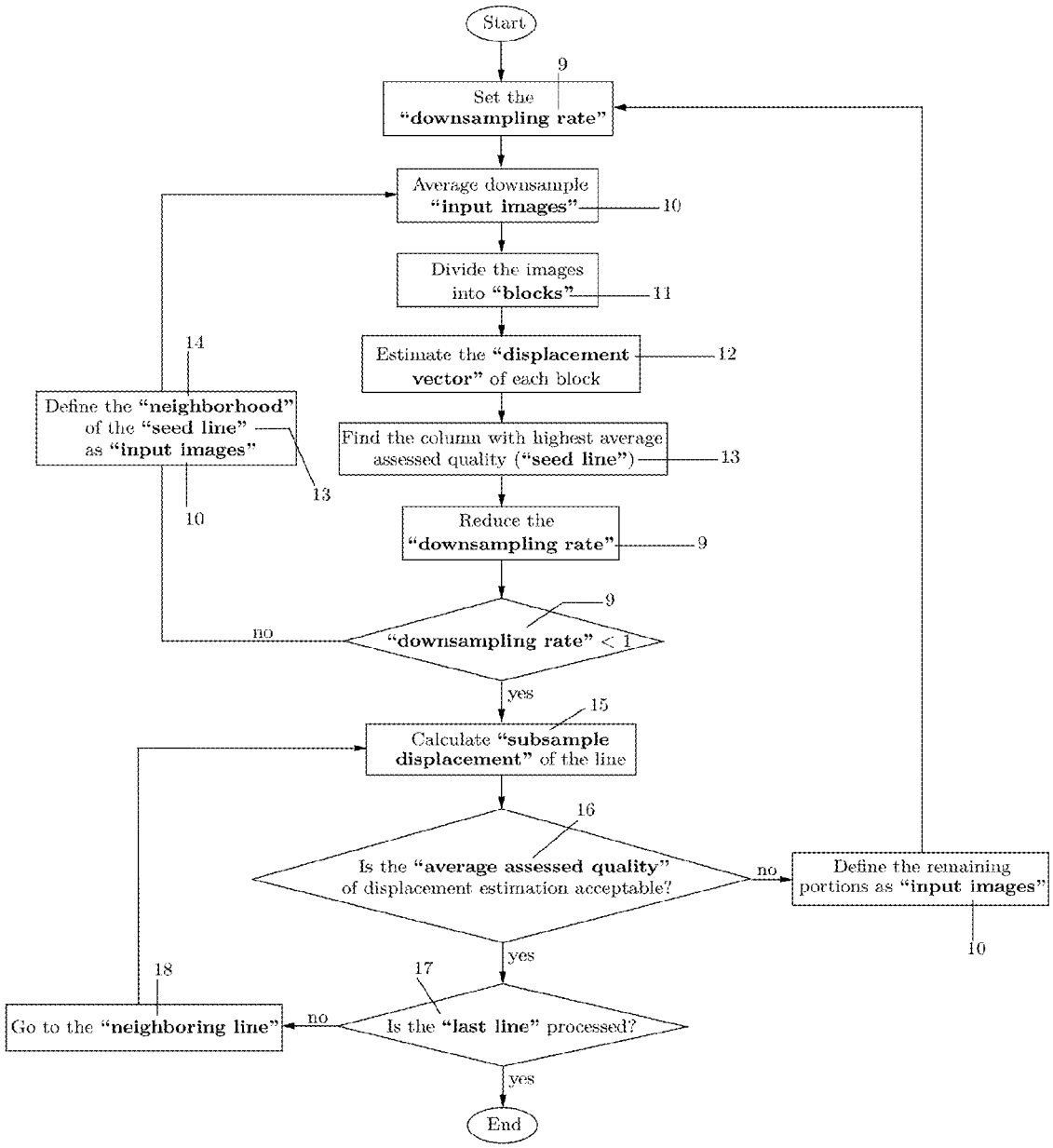
FIG. 2 shows a flowchart of a displacement estimation algorithm incorporated in the present invention.

FIG. 2 depicts the flowchart of a displacement estimation algorithm incorporated in the displacement estimator [4]. Upon initialization, the algorithm sets a downsampling rate [9] to downsample the input images [10] of the displacement estimation process. The input images [10] are extracted from the pre- and post-deformation images [3] loaded into the displacement estimator [4]. At first, the input images [10] exactly match the pre- and post-deformation images [3]. As the algorithm proceeds, limited portions of the pre- and post-deformation images [3] are selected as input images [10] to be loaded into the displacement estimation process, as will be described in the following.

Downsampling is performed to speed up the estimation process by reducing the size of input data. The downsampling rate [9] is initially set to a large value, and preferably a power of 2 (e.g., 8), and is gradually reduced to increase the precision of the results as the algorithm proceeds. The input data is averaged prior to downsampling to enhance the acquired information and reduce the noise effect on the downsampled data.

Figure 3:
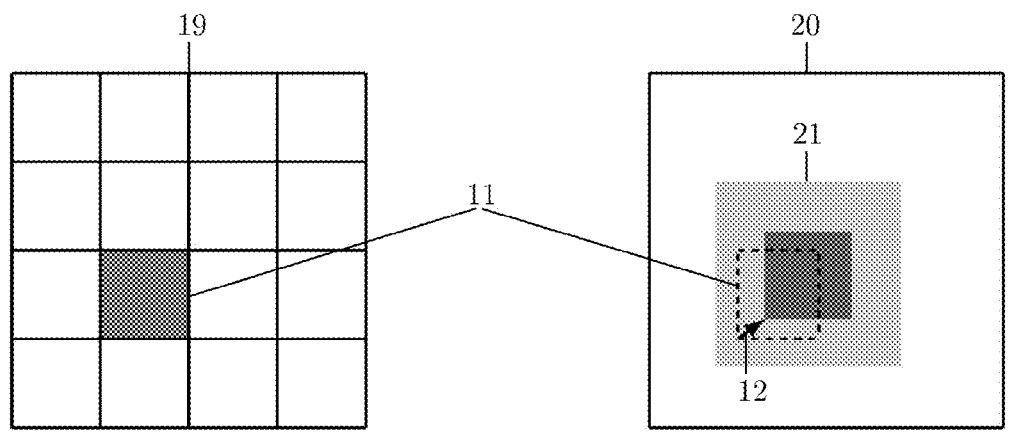
FIG. 3 shows a schematic of pre- and post-deformation input images divided into blocks. A search region is defined around each block in the post-deformation image to find the displacement vector of the corresponding block in the pre-deformation image.

Referring also to FIG. 3, the input images [10] are divided into blocks [11] after average downsampling, and a displacement vector [12] is estimated for each of the blocks [11], which determines the axial and lateral displacement for that block. For this purpose, a search region [21] is defined for every block and a similarity metric is calculated between the corresponding blocks [11] of the pre-deformation image [19] and post-deformation image [20] for all possible displacement vectors in the search region [21]. Examples of said similarity metric are the cross-correlation, or the sum of squared differences, or sum of absolute differences, etc. The displacement vector [12] that maximizes the similarity metric is selected as the estimated displacement vector [12].

The values of the similarity metric corresponding to the estimated vectors are utilized as a quality measure for the displacement map. Normally, the stress is applied in a direction aligned with an axis of a rectilinear array of pixels in strain imaging, and lines aligned with the direction of stress are conventionally "columns" and lines perpendicular to the direction of stress are conventionally "rows". For every column of blocks [11], the average value of the similarity metric is calculated and the column with the highest average value of quality measure is selected as the seed line [13] for the displacement map. Alternatively, the seed line [13] can be selected by performing the same procedure for every row of blocks [11]. However, using columns is preferred because it increases the speed of displacement estimation by limiting the search region [21] to the direction of applied stress. Hence, we use columns in a preferred embodiment.

After the appropriate seed line [13] is selected, the downsampling rate [9] is reduced, e.g. divided by 2 or any other number greater than unity, to gradually increase the resolution of input images [10] and subsequently enhance the precision of displacement estimation. If the downsampling rate [9] becomes less than 1 after reduction, it means that the displacement map with integer precision has been obtained, and downsampling is terminated. Subsequently, the algorithm proceeds to estimating subsample displacement [15] of the seed line [13], using any suitable technique including the aforementioned AM method proposed by Rivaz et al. When an initial estimate is used in a technique for calculating subsample displacement, for example in the iteratively reweighted least squares (IRLS) method by Rivaz et al., the integer displacement of the seed line [13] may be used as an initial estimate.

If the downsampling rate [9] remains above or equal to unity after being reduced, the algorithm confines the processed regions of input images [10] to the neighborhood [14] of the seed line [13], so that the size of processed data is reduced as the resolution is increased. This strategy improves the efficiency of the algorithm by preserving the speed of displacement estimation process.

Figure 4:
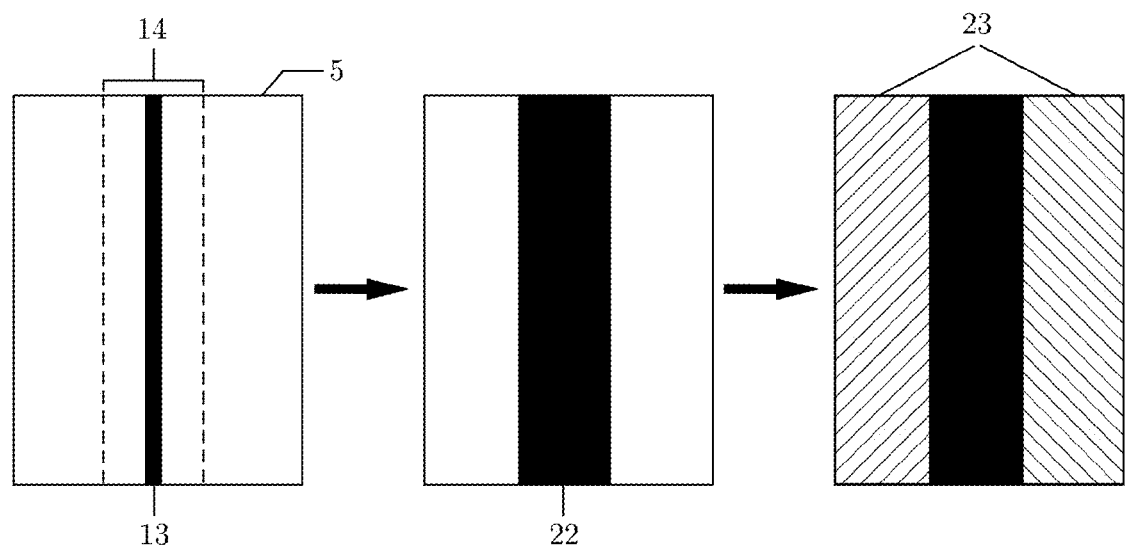
FIG. 4 shows a schematic of displacement map propagation from the initial seed line to the entire image.

Referring also to FIG. 4, the neighborhood [14] of the seed line [13] is defined as a limited number of columns of the input images [10] with the seed line [13] at the center. The neighborhood [14] is then loaded into the displacement estimation algorithm as the new input images [10] and the process is repeated until the downsampling rate [9] becomes less than unity.

After estimating the subsample displacement [15] of the seed line [13], the average assessed quality [16] of estimated displacement of the line is calculated using the aforementioned similarity metric. If the average assessed quality [16] is higher than a predefined threshold, the estimated displacements are considered acceptable. Subsequently, the algorithm estimates the corresponding subsample displacement [15] of the neighboring line [18] by using the displacement of the seed line [13] as an initial estimate. The neighboring line [18] is selected by comparing the average assessed quality [16] of the two adjacent columns (at the left and right sides) of the seed line [13]. Note that the average assessed quality [16] of each column was calculated prior to this step. The one with higher average assessed quality [16] is selected as the neighboring line [18] of the seed line [13], and the subsample displacement estimation is propagated through adjacent lines until a border line of the displacement map [5] is achieved, or the average assessed quality [16] falls below the threshold. The subsample displacement [15] of each line may be estimated by using the subsample displacement [15] of the previous adjacent line as the initial displacement estimation in the IRLS method. Afterwards, the algorithm proceeds through the other adjacent line of the seed line, until a processed portion [22] is generated for the displacement map [5].

The algorithm defines the remaining portions of initial input images [10] of which the subsample displacement [15]

is not estimated as the new input images [10] and restarts with a new downsampling rate [9] to find a new seed line [13]. The aforementioned subsample displacement [15] estimation process is repeated until the last line [17] of the input images [10] is processed, i.e., the complete displacement map [5] is obtained with subsample precision, leading the algorithm to finish. Several seed lines and corresponding processed portions [23] might be obtained during the displacement estimation process, according to the quality of the results. This approach enhances the robustness of the algorithm against the corrupt and decorrelated regions.

Figure 5:
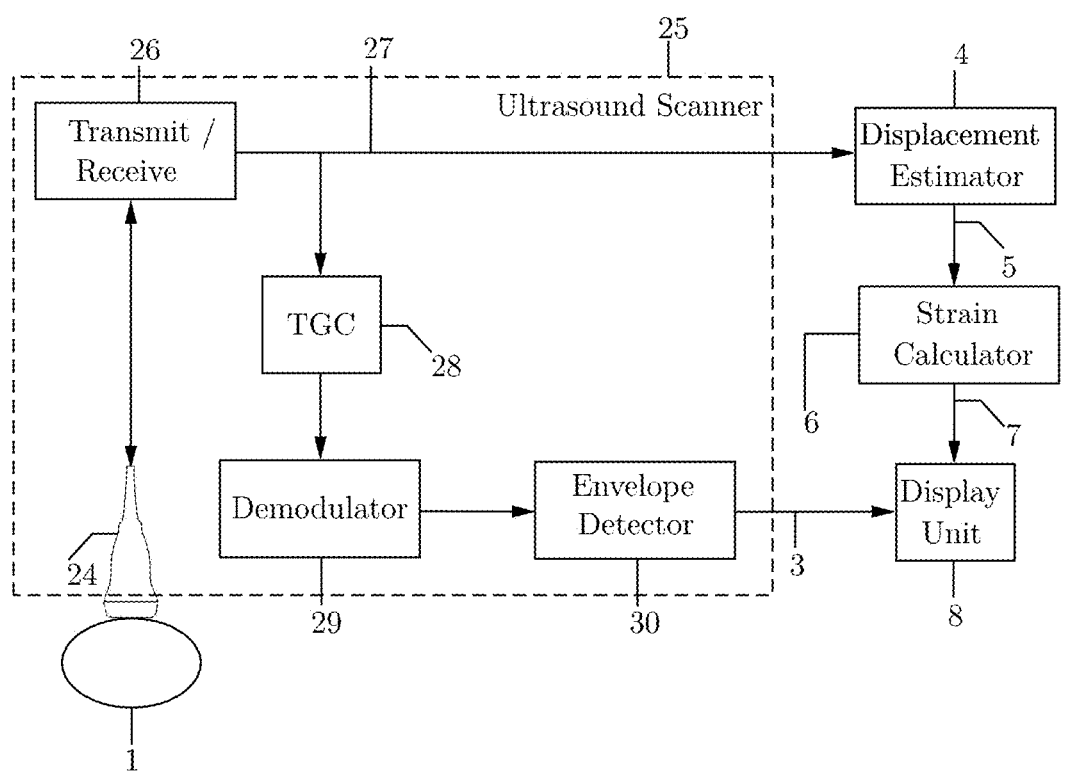
FIG. 5 shows a block diagram of one embodiment of the present invention incorporating an ultrasound imaging modality for freehand strain imaging.

FIG. 5 illustrates an embodiment of the present invention, wherein ultrasound imaging is employed for data acquisition. By way of exemplification and not a limitation, the ultrasound transducer [24] is utilized for compressing the object [1], as in freehand elastography. However, any other compression fixture can be used as an alternative to the ultrasound transducer [24] if available. The ultrasound scanner [25] includes a transmit/receive hardware [26] which operates the ultrasound transducer [24] to produce ultrasound waves and receive the corresponding raw RF echoes [27]. These echoes are loaded into a TGC block [28] which assigns appropriate weights to different parts of the raw RF echoes [27] according to the corresponding depth of each part, so that the differences in attenuation of raw RF echoes [27] are compensated. This process reduces the dynamic range of raw RF echoes [27] to facilitate the visualization of the signals. Output signals of the TGC block [28] are loaded into a demodulator [29] which extracts the corresponding baseband signals. These signals are then envelope detected by an envelope detector [30] to generate the final B-mode image [31]. Some other processes may be required prior to displaying B-mode data, such as scan conversion for converting the polar coordinate system to Cartesian if a sector transducer is used for data acquisition, and log-weighting to reduce the dynamic range of the output data to a level supported by the display unit [8]. Nevertheless, the output of the envelope detector [30] forms the essence of B-mode image [31] which is shown in the display unit [8] in real-time.

Referring still to FIG. 5, the strain estimation process is the same as that of FIG. 1. The input data loaded into the displacement estimator [4] in the embodiment shown in FIG. 5 is raw RF echoes [27]. It should be noted that the displacement estimation method in the present invention is independent of the input data. Irrespective of the source of input data, the strain estimation algorithm in this invention produces acceptable results.

Referring again to FIG. 5, the output data of the displacement estimator [4] is loaded into the strain calculator [6], which produces the strain map [7]. This image is shown side-by-side the real-time B-mode image [31] in the display unit [8].

Figure 6:
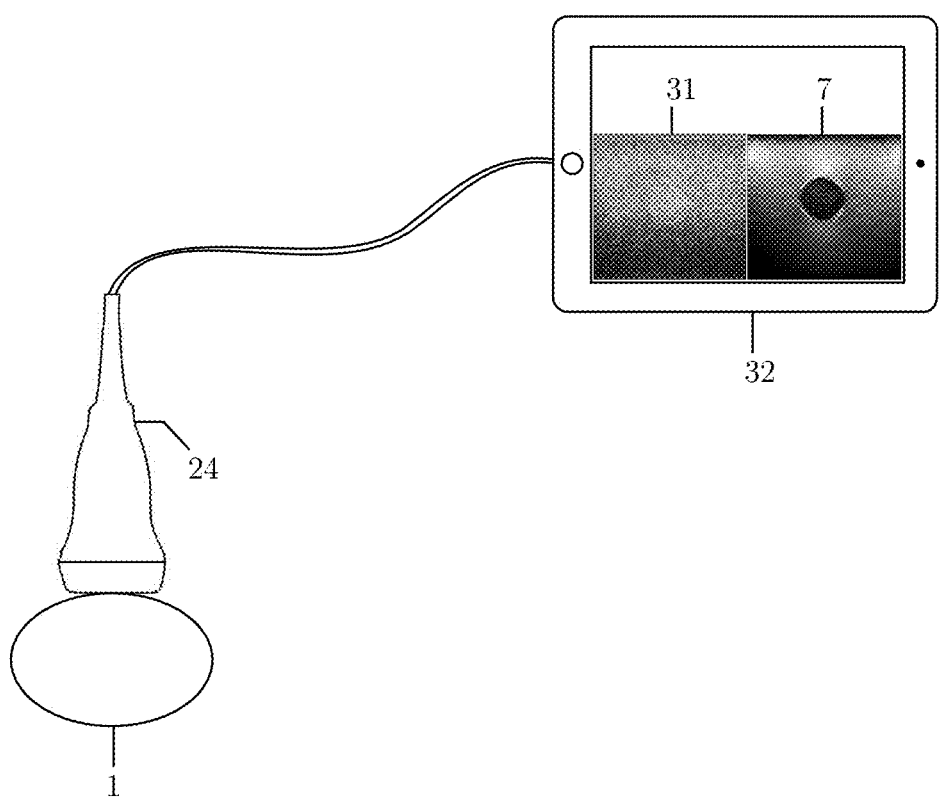
FIG. 6 shows an exemplary of freehand strain imaging apparatus, comprising an ultrasound probe connected to a tablet, according to the present invention.

FIG. 6 depicts an exemplary cost-effective system for freehand strain imaging by utilizing the present invention. The system consists of an ultrasound transducer [24] connected to a tablet PC [32]. Currently there are various commercial ultrasound probes that can be connected to personal computers, tablet PCs, or smart phones via a USB port. The ultrasound transducer [24] is used for both deforming the object [1] and acquiring ultrasound data of the pre- and post-deformation states of the object [1]. The ultrasound data is transferred to the tablet PC [32] and processed by the strain imaging method of the present invention to generate the strain map [7], which is displayed side-by-side the B-mode image [31]. This configuration forms an ultra-portable strain imaging device. The computational efficiency of the method in the present invention allows utilizing such cost-effective processing platforms for strain imaging. The tablet PC [32] can be substituted with any other conventional platform such as a personal computer, a laptop, or a smart phone. The present invention has the flexibility to adjust the visualization of B-mode image [31] and strain map [7] according to the display size of the platform, so that the details of both the B-mode image and the strain map can be simultaneously assessed to extract appropriate information. The user can decide whether to show the B-mode image [31] and strain map [7] side-by-side (in grayscale), as is more suitable for larger display units, or the strain map [7] is illustrated overlaid (in color) on the grayscale B-mode image [31], which is preferred in smaller display units.

Figure 7:
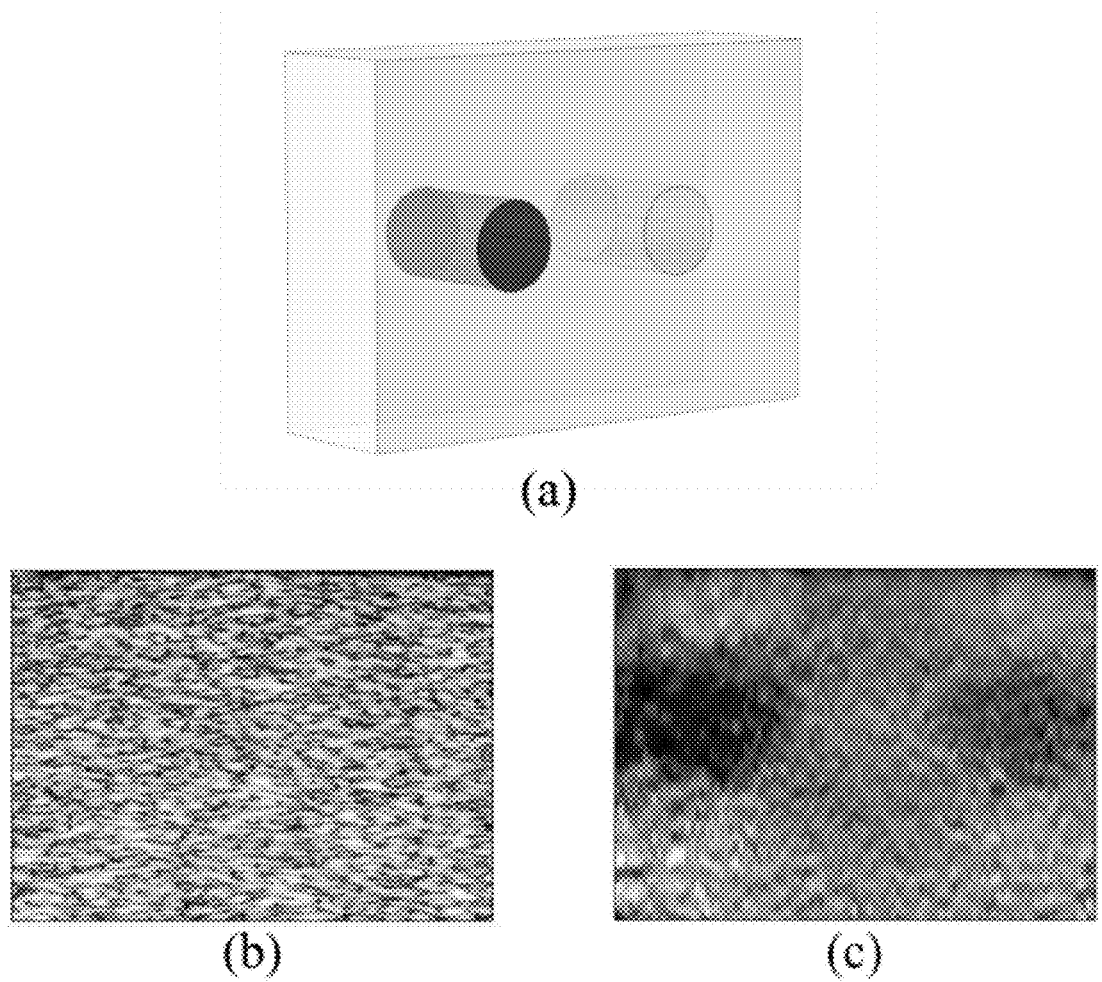
FIG. 7 shows an example of strain imaging according to the present invention. (a) A simulated phantom contains two cylindrical objects with different stiffness. (b) The objects are not visible in the B-mode image of the phantom (c) The two objects are observed in the strain image. The stiffer object is shown darker than the softer one.

FIG. 7 shows a sample strain map produced by utilizing the present invention in which cross correlation is chosen as the similarity metric in the displacement estimation algorithm. The downsampling rate was initially set to 8, and was step-by-step reduced through division by 2. Other aforementioned similarity metrics and downsampling procedures can also be incorporated to achieve similar results. FIG. 7($a$) shows a 36×10×25 mm simulated phantom containing two cylindrical objects (both 6 mm in diameter). The one in the left side is much stiffer than the other, with 1 MPa Young's modulus (simulating rubber). The Young's modulus of the right-side object is 90 KPa (simulating a biological lesion). The Young's modulus of the background is 30 KPa. FIG. 7($b$) shows the B-mode image of the phantom, in which no object is recognizable. On the contrary, the resultant strain map shown in FIG. 7($c$) clearly demonstrates and distinguishes the two objects. As shown in the figure, the stiffer inclusion is observed darker than the softer one.

Figure 8:
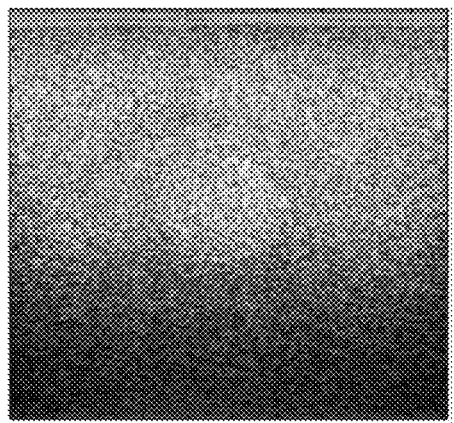
FIG. 8 shows an example of strain imaging according to the present invention. (a) The B-mode image shows a breast phantom with a malignant lesion in the middle. The lesion is clearly observed in (b) the strain image.
Figure 8:
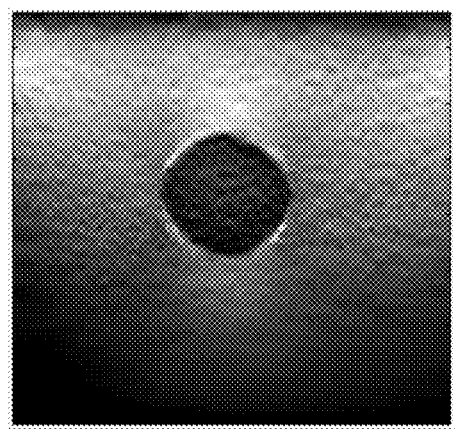

FIG. 8($a$) shows the B-mode image of a breast phantom (CIRS elastography phantom, Norfolk, Va.) containing a malignant lesion in the middle. The corresponding strain map is depicted in FIG. 8($b$). As shown in the figure, the malignant lesion is clearly observed in the strain map. This image shows that the strain imaging method of the present invention produces high quality results.

A major challenge in real-time strain imaging algorithms is robustness against undesired variations of input signals. Such variations occur mainly due to hand slips or excessive compression during freehand elastography, which increases decorrelation between pre- and post-deformation data. Since handling such decorrelations is not directly related to the imaging process, the corresponding computations are usually omitted or significantly reduced in real-time elastography to increase the speed of imaging. As a result, suitable conditions for achieving acceptable results by real-time algorithms becomes considerably more limited than those of offline methods. In other words, in general, real-time algorithms are much less robust than offline methods.

Figure 9:
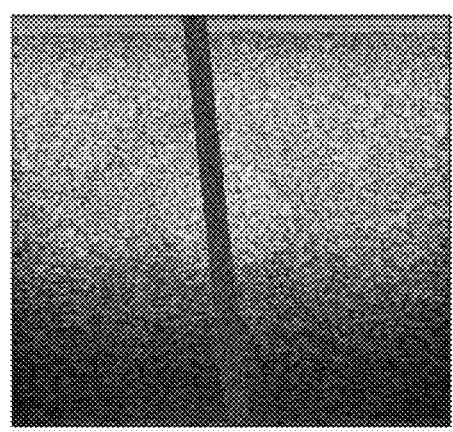
FIG. 9 shows the impact of corrupt regions on the performance of strain imaging in the present invention. (a) The B-mode image contains a band of corrupt data. (b) The corrupt region has negligible impact on other areas of the strain image.
Figure 9:
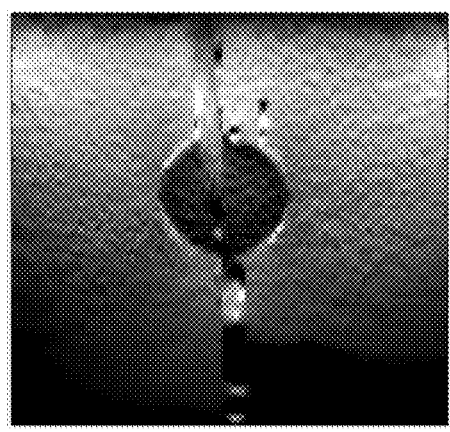

The robustness issue is considered and addressed in the present invention. As shown in FIG. 9, the values inside a band [33] in the B-mode image of FIG. 8($a$) are substituted with samples of white noise, to study the impact of decorrelated data on the imaging performance of the invention. Each sample of white noise has zero correlation with any other sample in the input images. Thus, the region inside the band [33] forms completely decorrelated data. The resulting strain map is illustrated in FIG. 9($b$). The image quality is similar to that in FIG. 8($b$) except for the region inside the band [33], which cannot be imaged because of the complete loss of input data. This implies that the decorrelated region has negligible impact on the image quality of the rest of data.

Figure 10:
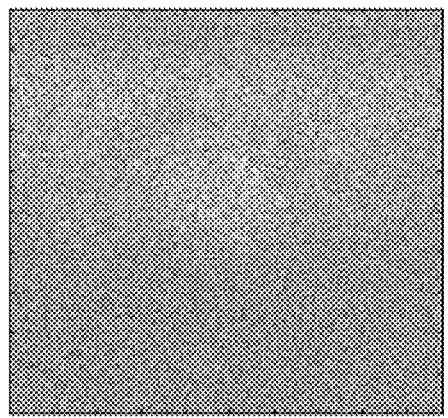
FIG. 10 shows the impact of highly decorrelated input data on strain imaging of the present invention. (a) Every sample of the B-mode image is added with a sample of a white noise distribution with an average level of five times that of the B-mode data. (b) The lesion is still recognized in the strain image.
Figure 10:
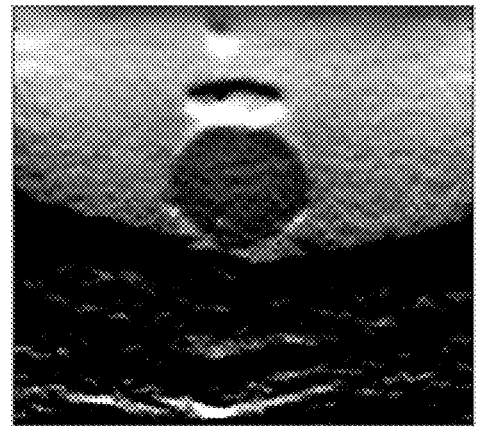

To study a further aspect of robustness in the present invention, each sample of the input data is added with a sample of white noise with an average level of five times that of the input data, to simulate a high degree of decorrelation that may be caused by applying too much compression to the object [1] during deformation. FIG. 10(a) shows the resulting B-mode image. The corresponding strain map obtained by utilizing the present invention is shown in FIG. 10(b). Although the quality of image is degraded because of high decorrelation, the lesion is still recognizable in FIG. 10(b). This establishes robustness of the present invention against high levels of decorrelation in input data.

Figure 11:
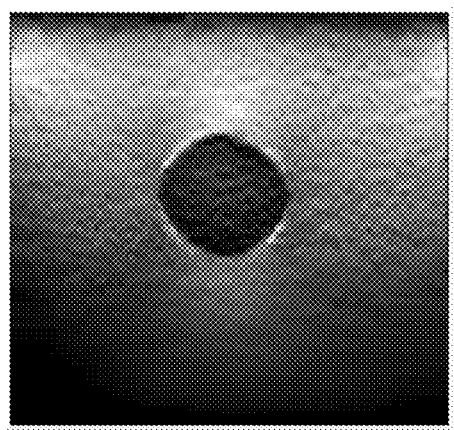
FIG. 11 shows the results of strain imaging using RF data and B-mode data in the present invention. (a) The strain map is generated using RF data. (b) B-mode data is used for strain imaging. Although the image contrast is slightly reduced, the lesion is clearly visible in the image.
Figure 11:
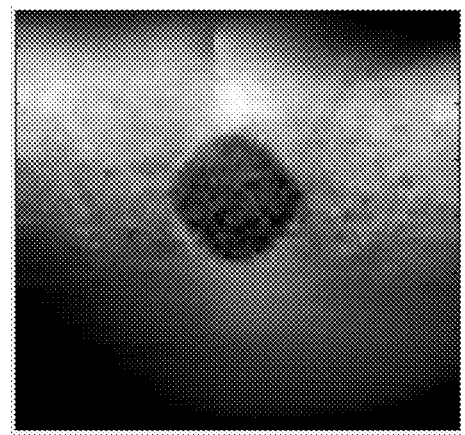

Finally, FIG. 11 compares the results of strain imaging in the present invention using RF data, as depicted in FIG. 11(a), and B-mode data, as shown in FIG. 11(b). The strain map in FIG. 11(b) has a slightly lower contrast than that in FIG. 11(a). But the quality of the image in FIG. 11(b) is still high and the lesion is clearly identifiable in the image. The advantage of this feature is the capability of utilizing anatomical images for strain imaging in the present invention, instead of RF data. Since anatomical images can be obtained with any type of medical imaging modalities, any of such systems can, in principle, be incorporated in the present invention, especially magnetic resonance imaging which is currently the second most commonly practiced modality for elastography after ultrasonic imaging.

What is claimed:

1. A method for real-time strain imaging, comprising:
   (a) applying compression on an object which is to be imaged with a view to deforming said object;
   (b) acquiring pre- and post-deformation images of said object;
   (c) extracting the displacement map of said object from said pre- and post-deformation images according to the steps of:
      (i) average downsampling said pre- and post-deformation images with a predefined downsampling rate;
      (ii) dividing said pre- and post-deformation images into blocks;
      (iii) estimating displacement vectors of said blocks;
      (iv) assessing the quality of said estimated displacement vectors using a similarity metric;
      (v) selecting a line of said blocks with the highest average value of said assessed quality as the seed line of said displacement map;
      (vi) step-by-step reduction of said downsampling rate until a lowest downsampling rate is reached, repeating the steps of downsampling images, dividing the images into blocks, and defining said seed line at each reduced downsampling rate;
      (vii) estimating subsample displacement of said seed line which corresponds to said lowest downsampling rate; and
      (viii) estimating subsample displacement for neighboring lines of each line for which the subsample displacement is estimated, starting with the neighboring lines of said seed line;
   (d) deriving the strain map of said object from said displacement map; and
   (e) displaying said strain map and said images side-by-side.

2. The method of claim 1 wherein the processed region of said pre- and post-deformation images is limited to the neighborhood of said seed line each time said downsampling rate is reduced until said downsampling rate goes below unity.

3. The method of claim 1 wherein the quality of said subsample displacement estimation of said neighboring lines is assessed using a similarity metric.

4. The method of claim 3 wherein said subsample displacement estimation is terminated if said quality of said subsample displacement estimation of said neighboring lines becomes lower than a predefined threshold, and extracting said displacement map, which includes selecting a new seed line, is resumed for the remaining portions of said pre- and post-deformation images for which subsample displacements are not estimated.

5. The method of claim 1 wherein a compression fixture is used for deforming said object.

6. The method of claim 5 wherein the process of said strain imaging is independent from the manner by which said compression fixture is utilized for deforming said object.

7. The method of claim 1 wherein said pre- and post-deformation images are acquired by an imaging modality.

8. The method of claim 7 wherein the process of said strain imaging is independent of said imaging modality.

9. An apparatus for real-time strain imaging, comprising:
   (a) an imaging system;
   (b) a displacement estimator connected to receive pre- and post-deformation images from the imaging system and to estimate a displacement map from the pre- and post-deformation images according to the steps of:
      i. average downsampling said pre- and post-deformation images with a predefined downsampling rate;
      ii. dividing said pre- and post-deformation images into blocks;
      iii. estimating displacement vectors of said blocks;
      iv. assessing the quality using a similarity metric for said estimated vector of said displacement map;
      v. selecting a line of said blocks with the highest average value of said assessed quality as the seed line of said displacement map;
      vi. step-by-step reduction of said downsampling rate until a lowest downsampling rate is reached, repeating the steps of downsampling images, dividing the images into blocks, and defining the seed line at each reduced downsampling rate;
      vii. estimating subsample displacement of said seed line as defined at the lowest downsampling rate; and
      viii. estimating subsample displacement for neighboring lines of each line for which the subsample displacement is estimated, starting with the neighboring lines of said seed line;
   (c) a strain calculator connected to receive said estimated displacement map from said displacement estimator and to produce a strain map from said estimated displacement map; and
   (d) a display unit connected to receive and display said strain map from said strain calculator.

10. The apparatus of claim 9 wherein the displacement estimator is configured to limit the processed region of said pre- and post-deformation images to the neighborhood of said seed line each time said downsampling rate is reduced until said downsampling rate goes below unity.

11. The apparatus of claim 9 wherein the displacement estimator is configured to assess the quality of said subsample displacement estimation of said neighboring lines using a similarity metric.

12. The apparatus of claim 11 wherein the displacement estimator is configured to terminate said subsample displacement estimation if said quality of said subsample displacement estimation of said neighboring lines becomes lower than a predefined threshold, and to resume extracting said displacement map, which includes selecting a new seed line, for the remaining portions of said pre- and post-deformation images for which subsample displacements are not estimated.

13. The apparatus of claim 9 in which said display unit is also configured to receive said pre- and post-deformation images and to display said pre- and post-deformation images side-by-side with said strain map.

14. The apparatus of claim 9 in which the pre- and post-deformation images are obtained by imaging an object before and after applying compression on said object with a view to deforming said object.

15. The apparatus of claim 14 wherein said compression is applied to said object via a part of said imaging system.

16. The apparatus of claim 14 wherein said pre- and post-deformation images are ultrasound B-mode images.

17. The apparatus of claim 16 in which the images are sent to said displacement estimator via an interface unit.

18. The apparatus of claim 9 in which said imaging system is an ultrasound transceiver.

19. The apparatus of claim 9 in which said displacement estimator and strain calculator are implemented in a host computer.

20. The apparatus of claim 19 wherein said imaging system is connected to said host computer via an interface unit.

* * * * *